United States Patent

Hammen et al.

[11] Patent Number: 5,927,562
[45] Date of Patent: Jul. 27, 1999

[54] DEVICE FOR DISPENSING A FLOWABLE SUBSTANCE

[75] Inventors: Klaus Hammen, Gilching; Gerd Brandhorst, Landsberg, both of Germany

[73] Assignee: Thera Patent GmbH & Co. KG Gesellschaft Fuer Industrielle Schutzrechte, Seefeld, Germany

[21] Appl. No.: 08/966,018

[22] Filed: Nov. 7, 1997

[30] Foreign Application Priority Data

Nov. 11, 1996 [DE] Germany .......................... 296 19 558

[51] Int. Cl.⁶ ..................................................... A61C 5/04
[52] U.S. Cl. .......................... 222/327; 222/386; 222/533; 433/90
[58] Field of Search .................................... 222/327, 386, 222/533, 575; 433/90

[56] References Cited

U.S. PATENT DOCUMENTS

| | | | |
|---|---|---|---|
| 4,295,828 | 10/1981 | Rudler | 433/90 |
| 4,330,280 | 5/1982 | Dougherty et al. | 433/90 |
| 4,813,871 | 3/1989 | Friedman | 222/386 |
| 5,022,563 | 6/1991 | Marchitto et al. | 222/327 |
| 5,129,825 | 7/1992 | Discko, Jr. | 433/90 |
| 5,722,830 | 3/1998 | Brandhorst et al. | 433/90 |
| 5,749,498 | 5/1998 | Lavoie et al. | 222/533 |

*Primary Examiner*—Philippe Deraksham
*Attorney, Agent, or Firm*—Foley & Lardner

[57] ABSTRACT

A device suited for dispensing a dental substance comprises a cartridge 20 for receiving the substance, with a curved dispensing nozzle 22 disposed at the front end and a flange 21 of octagonal cross-section provided at the rear end of the cartridge. The flange 21 serves to engage a slide-in socket 16 of an applicator 10 which includes a piston rod 12 for advancing a dispensing piston 23 disposed in the cartridge 20. In the retracted position of the piston rod 12, the cartridge 20 may be laterally inserted into the slide-in socket 16 of the applicator 10. The socket has two parallel walls spaced by a distance which is between the largest and the smallest diameter of the octagonal flange 21. The material of the flange 21 and/or the material forming the slide-in socket 16 is resilient so that the cartridge 20 may be stepwise rotated about the axis of the piston rod 12 with respect to the applicator 10 without requiring the piston rod 12 to be withdrawn and the cartridge 20 to be removed from the slide-in socket and re-inserted in a new orientation.

8 Claims, 2 Drawing Sheets

DEVICE FOR DISPENSING A FLOWABLE SUBSTANCE

BACKGROUND OF THE INVENTION

U.S. Pat. No. 5,722,830 describes a container for storing and dispensing a flowable substance, specifically a dental substance, comprising a cartridge for receiving the substance, with a dispensing nozzle in the form of a curved tube being connected to the font end of the cartridge and the rear end of the cartridge having a flange for inserting into an applicator. The flange has preferably the shape of a hexagonal prism which, as described in the above application is intended to make sure that when a cartridge is placed in the applicator, the dispensing end of the nozzle maintains its orientation with respect to the applicator. This is of significance especially when small amounts of the substance contained in the cartridge are to be precisely dispensed at confined locations, as is the case with dental substances that are to be applied directly to a location of treatment, e.g. to be filled into a tooth cavity.

SUMMARY OF THE INVENTION

The present invention relates to a development of the dispensing device disclosed in the above application, with the object of improving the handling thereof.

To meet this object, the invention provides a device for dispensing a flowable substance, comprising a cartridge for receiving the substance, the cartridge having a front end and a rear end and defining an axis, the cartridge including a dispensing piston, a dispensing nozzle connected to the front end and having a dispensing end extending at an angle with respect to the axis, and a prismatic flange provided at the rear end, and an applicator including a piston rod for advancing the dispensing piston in the cartridge and a receiving portion for receiving the flange, the receiving portion having a cross-sectional shape other than circular, the smallest diametric dimension of the receiving portion having a value between the smallest and the largest diametric dimension of the prismatic flange, wherein the material of the flange and/or of the receiving portion is resilient so as to permit stepwise rotation of the cartridge relative to the applicator.

In accordance with the invention—just as in the prior art—the cartridge is prevented in use from inadvertently rotating with respect to the applicator; on the other hand, an intended change of the relative position between cartridge and applicator, thus a change in the dispensing angle, can be performed by exerting a small force during operation and re-insert it in a different orientation. For the practical handling, the device is therefore still more readily adapted to the respective requirements.

In a preferred embodiment, the cross-section of the flange has the shape of a regular polygon, specifically an octagon. This shape is suitable because it provides not only a sufficient diametric difference between opposite corners, on the one hand, and opposite faces, on the other hand, thus a pronounced latching action, but also a variation of the rotational position in practical small steps.

The receiving portion is preferably constituted by a slide-in socket which is open transversely of the axis of the piston rod, with the smallest diametric dimension of the socket being defined by a pair of opposite parallel walls. This structure makes the device simple to assemble by the user.

In accordance with other aspects of the invention, which are advantage from the manufacturing standpoint, the piston rod extends through a guide bore provided in a handle part of the applicator, the end of the piston rod adjacent the dispensing piston having a stop member the outer dimension of which is larger than the diameter of the guide bore. The stop member may be formed by a stamp-deformed front end portion of the piston rod. The handle part preferably has a section connected to the receiving portion and being larger than the guide bore, for receiving the stop member.

A device which is particularly suited with respect to the practical handling is obtained if the rear end of the piston rod remote from the dispensing piston carries a thumb-pushing member, and the handle part is provided with two lateral finger holds.

DETAILED DESCRIPTION OF A PREFERRED EMBODIMENT

Figure 1:
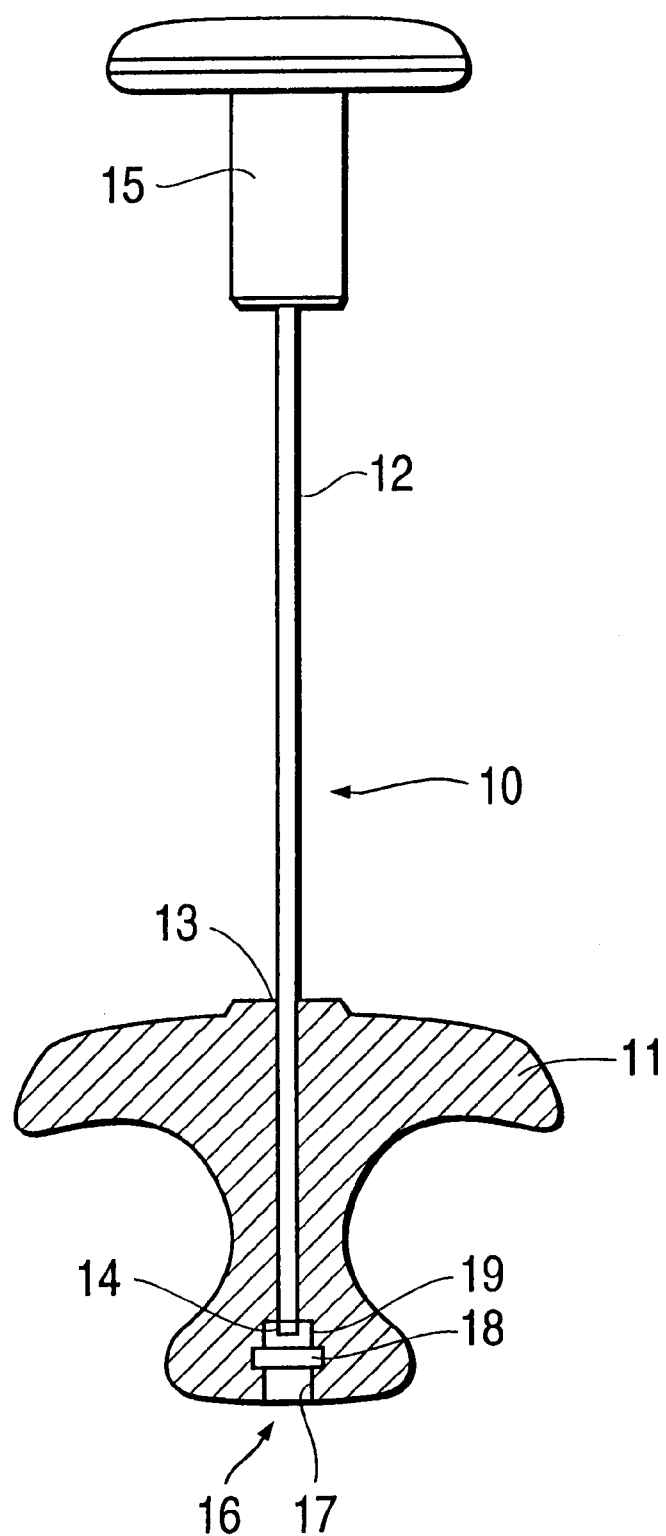
FIG. 1 shows an applicator with a handle part, cut along the axial direction.

According to FIG. 1, the applicator 10 consists of a handle part 11 and a piston rod 12. The piston rod 12 extends through a guide bore 13 of the handle part 11; the front end (the lower end in FIG. 1) of the piston rod is provided with a stop member 14, and its rear end carries a thumb-pushing member 15.

The handle part is formed with a slide-in socket 16 which includes an outer receiving portion 17, a middle receiving portion 18 and an inner portion 19. The three portions 17, 18 and 19 are open transversely of the axis (in FIG. 1 towards the viewer), each portion having a semi-cylindrical bottom with two opposite parallel wall sections extending from the bottom. The middle portion 18 has a larger diameter than the outer and inner portions 17, 19.

The stop member 14 is constituted by the front end portion of the piston rod 12; the cross-section of the stop member 14 has been enlarged by stamping with respect to the cross-section of the guide bore 13 so that the piston rod 12 cannot be withdrawn from the handle part 11. The axial length of the stop member 14 is somewhat shorter than that of the inner portion 19 of the socket 16.

Figure 2:
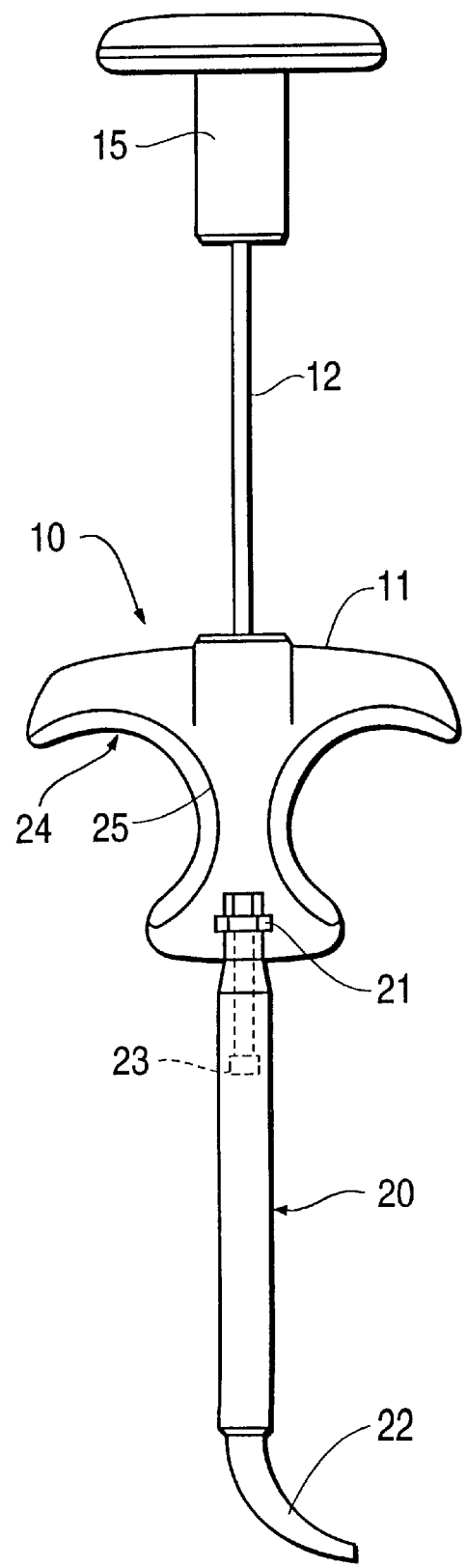
FIG. 2 shows the applicator with a cartridge inserted.

In FIG. 1, the piston rod 12 is shown in a condition in which it has been retracted as far as possible with respect to the handle part 11. In this condition, the portions 17 and 18 of the socket are laterally free. A cartridge 20 may be inserted into these portions in such a way that a flange 21 provided at the rear cartridge end engages the middle portion 18 of the socket 16. This condition is shown in FIG. 2.

The flange 21 is shaped as a regular octagonal prism, with the diametric dimension between two opposite faces of the prism being somewhat smaller than the spacing between the opposite, parallel wall sections of the middle portion 18 of the socket 16. Since the cylindrical rear end of the cartridge 20 also has a somewhat smaller diameter than the outer receiving portion 17, the cartridge 20 may be readily inserted laterally into the slide-in socket 16 and placed in the position shown in FIG. 2.

The diametric dimension between two opposite edges of the octagonal-prismatic flange 21 is slightly larger than the spacing between the opposite wall sections of the middle portion 18 of the socket 16. The material of the cartridge 20 and of the flange 21 integral therewith is resiliently de-formable so that the cartridge can be rotated, by exerting a moderate force, about its longitudinal axis with respect to the handle part 11 of the applicator 10. In addition or alternatively, the desired resiliency may be provided by accordingly selecting the material of the handle part 11.

For applying the said force, the cartridge 20 may be held by gripping a curved dispensing nozzle 22 provided at the front end of the cartridge. During rotation, a position is overcome in which two edges of the octagonal-prismatic flange 21 oppose the parallel wall sections of the middle portion 18 of the socket 16. On further rotation, the cartridge will lock into a position which is rotated 45° with respect to the starting position and in which again two faces of the flange 21 oppose the wall sections of the middle portion 18 of the socket 16.

It is essential that the described rotation can be performed while the piston rod 12 engages in the cartridge 20 and has its stop member 14 (the diameter of which is smaller than the inner diameter of the cartridge 20) abutting the rear end of a dispensing piston 23 provided inside the cartridge 20.

Thus, changing the rotational position between the applicator 10 and the cartridge 20 during use does not require the piston rod 12 to be retracted, the cartridge to be removed from the slide-in socket 16 and to be re-inserted in a new orientation. Instead, the rotational position may be changed immediately before a dispensing step—or even during the same—after the device has already been placed in its final condition and the end of the dispensing nozzle 22 has reached the location of treatment.

The handle part 11 is formed with two opposite finger holds 24 which are provided with enlarged gripping flanges 25 for better engagement by the index and middle finger. The applicator may thus be operated by one hand with the other hand being free to rotate the cartridge 20 with respect to the handle part 11 if necessary.

In the case of dental substances, such as tooth stopping substances to be directly dispensed into a tooth cavity, the cartridge has an inner diameter of, e.g., 1.5 to 5 mm, preferably approximately 2.5 mm, and the dispensing end of the curved converging dispensing nozzle 22 as an inner diameter of, e.g. 1.5 to 3 mm, preferably approx. 2 mm. The handle part 11 and the thumb-pushing member 15 are made of synthetic resin by injection moulding. The piston rod 12 is preferably made of a spring steel wire injection moulded with the thumb-pushing member 15.

We claim:

1. A device for dispensing a flowable substance, comprising a cartridge for receiving the substance, said cartridge having a front end and a rear end and defining an axis, said cartridge including a dispensing piston, a dispensing nozzle connected to said front end and having a dispensing and extending at an angle with respect to said axis, and a prismatic flange provided at said rear end, and an applicator including a piston rod for advancing said dispensing piston in said cartridge and a receiving portion for receiving said flange, said receiving portion having a cross-sectional shape other than circular, the smallest diametric dimension of said receiving portion having a value between the smallest and the largest diametric dimension of said prismatic flange, wherein the material of at least one of said flange and receiving portion is resilient so as to permit stepwise rotation of said cartridge relative to said applicator.

2. The device of claim 1, wherein the cross-section of said flange has the shape of a regular polygon.

3. The device of claim 2, wherein said polygon is an octagon.

4. The device of claim 1, wherein said receiving portion is constituted by a slide-in socket which is open transversely of said axis, said socket having a pair of opposite parallel walls which define the smallest diametric dimension of said socket.

5. The device of claim 1, wherein said applicator includes a handle part provided with a guide bore, said piston rod extending through said guide bore, said piston rod having an end provided with a stop member adjacent said dispensing piston, the outer dimension of said stop member being larger than the diameter of said guide bore.

6. The device of claim 5, wherein said stop member is formed by a stamp-deformed end portion of said piston rod.

7. The device of claim 5, wherein said handle part has a portion for accommodating said stop member, said accommodating portion being connected to said receiving portion and being larger than said guide bore.

8. The device of claim 1, wherein said handle part includes a pair of lateral finger holds, and said piston rod has a thumb-pushing member provided at a rear end of said piston rod.

* * * * *